United States Patent [19]
Rodler

[11] 3,958,577
[45] May 25, 1976

[54] APPARATUS FOR TREATMENT WITH SUM CURRENTS

[76] Inventor: Hans Rodler, Karntnerstrasse 161, 8053 Graz-Neuhart, Austria

[22] Filed: Nov. 21, 1972

[21] Appl. No.: 308,344

[30] Foreign Application Priority Data
Nov. 22, 1971  Austria .............................. 10037/71

[52] U.S. Cl. .......................................... 128/420 A
[51] Int. Cl.² ........................................ A61N 1/36
[58] Field of Search ............... 128/419 R, 420, 421, 128/422, 2.06 A, 2.06 B, 2.06 R, 2.1 R, 2.1 Z; 330/29, 145, 85

[56] References Cited
UNITED STATES PATENTS

| | | | |
|---|---|---|---|
| 2,673,559 | 3/1954 | Fawcett | 128/2.06 B |
| 2,979,667 | 4/1961 | Paschal | 330/29 |
| 3,523,539 | 8/1970 | Lavezzo | 128/422 |
| 3,708,754 | 1/1973 | Diehl | 330/29 |

FOREIGN PATENTS OR APPLICATIONS

| | | | |
|---|---|---|---|
| 850,926 | 9/1952 | Germany | 128/2.06 B |
| 1,130,680 | 10/1956 | France | 128/420 A |

*Primary Examiner*—William E. Kamm
*Attorney, Agent, or Firm*—Ernest G. Montague

[57] ABSTRACT

An apparatus for producing interference and beat-currents in a selectable point of the body, particularly for electrotherapy on the human body, which comprises at least two pairs of electrodes adapted to be applied to the human body. Each of the pairs of electrodes has associated therewith an output amplifier. The latter supplies independently selectively pulse and alternating current for each pair of the electrodes. A voltage proportional in amplitude to the current flowing through the patient is taken. The voltage relates mathematically each individual setting voltage with a common setting and is subtracted. The difference voltage is produced separately for each circuit and used for the amplification control on the corresponding of the amplifiers, and the voltage is so polarized that an increase in patient current resulting in a decrease of the amplification and an increase in the joint voltage resulting in an increase of the amplification.

6 Claims, 4 Drawing Figures

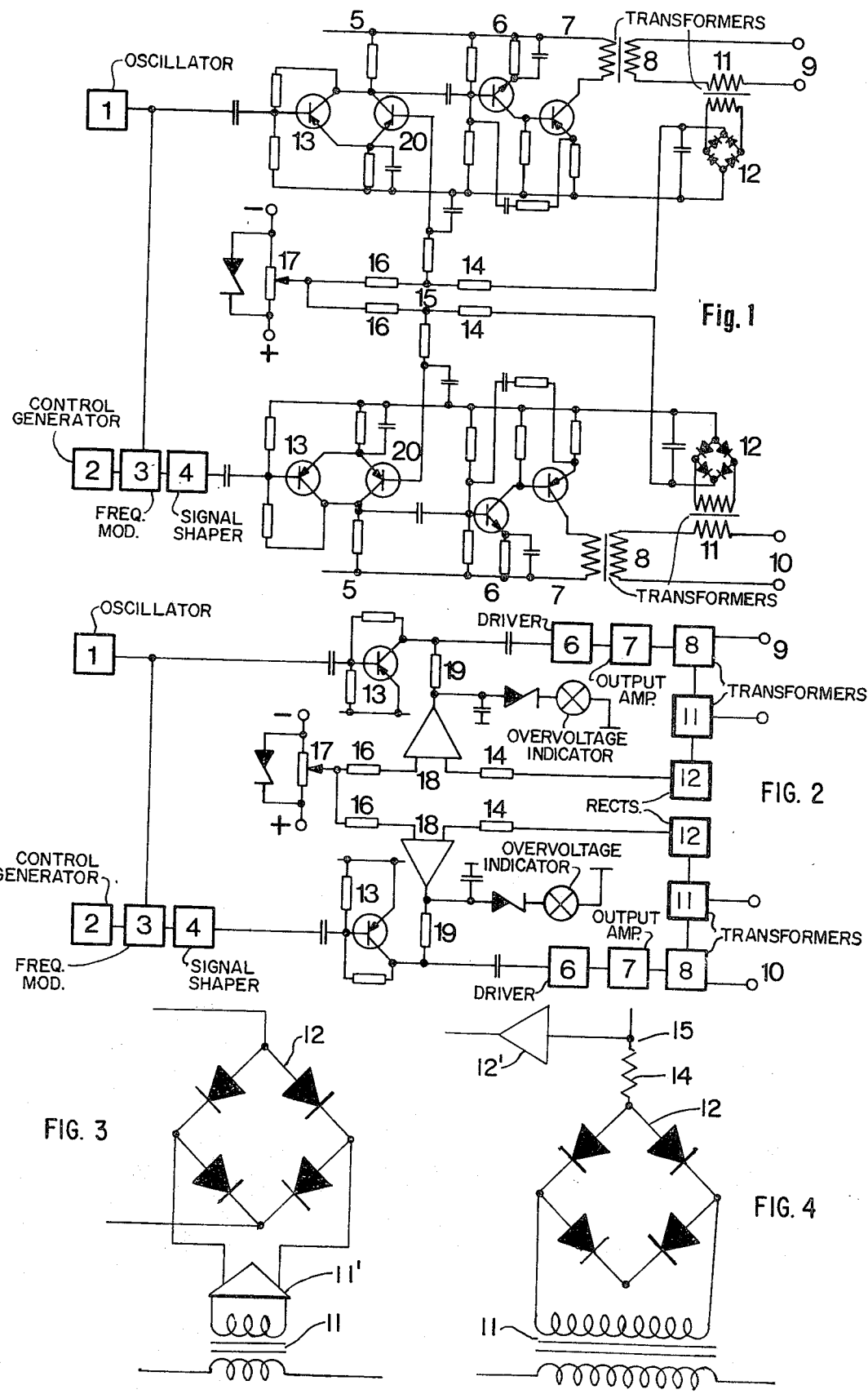

APPARATUS FOR TREATMENT WITH SUM CURRENTS

The present invention relates to an apparatus for treatment with sum currents, in which the output stages are regulated by an automatic current control in such a manner, that the same large current flows in each circuit and the size of the current is adjustable by a comparison voltage.

In the previously known instruments, the circuits had to be brought manually to the same value by a balancing circuit. This adjustment is cumbersome and inaccurate and can change due to variations in electrode resistances. Furthermore, there is the possibility that a part of the current of the one circuit will flow over the second circuit and in this way cause interference phenomena at the electrodes. It is, however, more favorable if interference occurs only at some depth. By a switchable compensation circuit containing a capacitor and a resistor, it was attempted to eliminate this defect in the previous arrangements. This method is only imperfect and furthermore requires a cumbersome switching process.

It is one object of the present invention, to provide an apparatus for treatment with sum currents. The apparatus for the production of interference currents at a selectable point of the body, particularly for elctrotherapy on the human body, comprises at least two pairs of electrodes applied to the body, there being associated with each pair of electrodes an output amplifier which supplies independently pulse or alternating current for each pair of electrodes. There is taken for each pair of electrodes a voltage which is proportional in amplitude to the current flowing through the patient, which voltage mathematically couples each individual setting voltage with a common setting voltage, and preferably is subtracted, in which connection the difference voltage occurring separately for each circuit is used in known manner for the amplification control at the corresponding amplifier, the voltage being of such polarity here that an increase in the current through the patient effects a reduction of the amplification, while an increase of the common voltage effects an increase in the amplification.

The apparatus for treatment with sum currents can be constructed so that the primary winding of a transformer is connected in series to each circuit formed by a pair of electrodes, the transformer on its secondary side supplying via rectifiers the current-proportional voltage which is conducted over a resistor to a control line which in its turn is connected via a resistor with a potentiometer acted on by a D.C. voltage, the difference voltage occurring on the control line being used to conrol the amplification of the amplifier.

In this way a voltage which is proportional to the current passing through is obtained for each circuit independently at the secondary winding of the series transformer.

By the rectification and feeding via a resistor of the control line, a dependable uncoupling is assured so that no undesired oscillation phenomena can occur. The potentiometer which is acted on by D.C. voltage supplies an adjustable voltage of opposite polarity to the current-dependent voltage which is fed via a resistor also to the control line. Instead of this resistor, diodes or other components can, of course, also be used.

Due to the fact, that the comparison voltage and the current-proportional voltage are of opposite polarity, the difference of the two voltages appears at the coupling point of the two resistors. This difference voltage is then used in known manner, for instance by a transistor connected in parallel to the amplifier or by a field-effect transistor connected in series with the amplification response in order to control the amplification.

If the resistance of the patient becomes less, then an increase of current in the patient circuit leads to a change in difference voltage which in its turn reduces the amplification and thereby adjusts the original patient current. If, on the other hand, the comparison voltage is increased, this effects a change in the control voltage in reverse direction and the amplification becomes higher and the patient current thus higher. In this way a patient current which is approximately proportional to the comparison voltage is produced. Since all patient circuits are compared with the same comparison voltage, all patient circuits must necessarily conduct the same current. Thus there flows over the patient electrodes a current which depends only on the adjustable comparison voltage. With this adjustable comparison voltage one can, by means of a regulator, regulate simultaneously the current intensity of all patient circuits. If the patient current drops by an increase in the electrode resistances, the control voltage occurring increases the amplification and thus increases the patient current to the original value. If a current now flows from one patient circuit into the second, then, depending on the phases of the current with respect to each other, the current-dependent control voltage will also be changed and brought back to the original current intensity in the circuit in question.

By this process, beats in the electrode region are prevented and the interference phenomena are in addition amplified in the depth of the object.

In accordance with the present invention, the difference voltage for the control can also be formed by connecting the current proportional voltage to one input of a difference amplifier and the comparison voltage to the other input of the difference amplifier via resistors, the output of the difference amplifier forming the control voltage. In this way there is obtained an amplification of the control process so that an even greater constancy of current can be obtained.

In accordance with the present invention, in order to increase the control effectiveness, an amplifier can also be provided between the secondary winding of the series transformer and the rectifier circuit. The amplifier can in this case be connected as an alternating current amplifier.

In accordance with the present invention, the control process can also be increased by connecting a D.C. amplifier between control line and controlled amplifier. This arrangement in its turn has the advantage that the coupling processes between output and input are less critical. The advantage of the invention resides in that on the one hand a constant current circuit is obtained, in which connection, of course, by corresponding decrease of the load-dependent voltage, a constant voltage circuit can also be obtained.

Furthermore, the result is hereby obtained that several circuits can be controlled simultaneously and in the same direction with a single controller, the currents being compared electronically with each other and therefore the same current must flow in each patient circuit within certain limits. In addition to this, however, currents flowing from one circuit to the other must also be taken into consideration, not only on basis of their amplitude, but also their phases, so that beat phenomena are avoided at the electrodes and beat phenomena in the depth of the point of intersection are further increased. Since after exceeding a certain voltage the arrangement can come out of step, an overvoltage indicating device is connected in accordance with the invention to the control line, said device indicating when the control voltage exceeds a given amount. With these and other objects in view, which will become apparent in the following detailed description, the present invention, which is shown by example only, will be clearly understood in connection with the accompanying drawings, in which:

FIG. 1 is a control arrangement without additional amplifier;

FIG. 2 is a control arrangement with additionally installed difference amplifier; and FIGS. 3 and 4 show circuit modifications.

Referring now to the drawing, the circuit as disclosed in FIG. 1, comprises an oscillator 1, which charges the patient circuit 9 on the one hand via the control stage 5 of the driver stage 6 and the output amplifier 7 via the output transformer 8. In the series with the patient circuit 9 there is connected a transformer 11 whose secondary winding leads to a rectifier circuit 12. This rectifier circuit is connected on the one hand to ground and on the other hand via a resistor 14 with the control line 15 which is simultaneously acted on via a resistor 16 by a potentiometer 17. The voltages are so polarized that they counteract each other in the control line. This control line now leads via a resistor to a control transistor 20 which lies in parallel to an amplification transistor 13. If the negative voltage of the rectifier 12 becomes larger, since the patient current in 9 increases due to smaller patient resistance, a negative difference voltage is then produced in the control line. The flow of current in the control transistor 20 becomes greater. This results in a reduction in the amplification of the transistor 13 so that the current in 9 is brought back to the original value. If a higher voltage is adjusted by means of the potentiometer, then the control voltage will change towards the positive region. The transistor 20 will conduct less current and will dampen the amplification transistor less, so that the amplification in 5 will become greater and the patient current in 9 will increase thereby. At the same time, a frequency-modulated oscillation will be produced from the oscillator 1 via a frequency modulator 3 and the control generator 2 through signal shaper 4, which oscillation also controls an arrangement 5, 6, 7, 8, 10, 11, 12 in the same form.

Referring to FIG. 2, the circuit comprises again a low-frequency oscillator 1 which supplies the patient current via the control stage 5 of the driver stage 6 and the output stage 7 via the transformers 8, 11 and the rectifier circuit 12. In this case, a control amplifier 18 which is developed as difference amplifier is controlled via the resistor 14. The control amplifier controls the transistor 13 via the resistor 19. The second side of the difference amplifier is controlled via the resistor 16 by the potentiometers 17. The difference amplifier is in this case connected in such a manner that an increase in voltage through the current-dependent circuit 12 leads to a reduction in voltage at the output of the difference amplifier, so that the transistor 13 receives less voltage and thus has a smaller amplification and brings the current back to the original value in 9. An increase in voltage in the potentiometer results in an increase in voltage at the output of the difference amplifier and thus in an increase in amplification in the control stage 5. At the output of the difference amplifier there is furthermore connected via a zener diode a signal device, preferably a luminescence diode, which, by exceeding a given voltage, gives off a warning signal.

From the generator 1 furthermore, via the frequency modulator 3 and 2, as well as the curve-shaping member 4, there is supplied a second amplification arrangement having a phase-shifted oscillation, this amplifier consisting also of a control stage which is controlled by a difference amplifier 18, a driver stage 6, an ouput stage 7 and the switch unit 8, 11 and 12. A useful-current output 10 in this case is also provided.

As shown in FIGS. 3 and 4, an amplifier 11' can be disposed between the secondary winding of each of said transformer 11 and the rectifiers 12 or at 12' between each control line and the respective amplifier.

While I have disclosed a plurality of embodiments of the present invention, it is to be understood that these embodiments are given by example only.

I claim:

1. An apparatus for producing interference and beat-currents in a selectable point of the body, particularly for electrotherapy on the human body, comprising
   at least two circuits having two pairs of electrodes, respectively, adapted to be applied to the human body,
   said circuits each having a controllable output amplifier means controlling its output currents by controlling its amplification and for maintaining the output currents at a constant value, each of said output amplifiers being operatively connected to one of said pairs of electrodes, means connected to said amplifier means for supplying independently both pulsed and alternating current to said pairs of electrodes,
   sensing means operatively connected to each of said pairs of electrodes for providing an individual voltage proportional in amplitude to current flowing through the patient,
   means for providing a common setting voltage,
   common controller means connected to said amplifier means for controlling the amplification thereof, said controller means receiving said voltages for mathematically relating each of said individual voltages with said common setting voltage and for producing a difference voltage separately for each of said circuits,
   said controller means including means for polarizing said difference voltage such that an increase in current through each pair of electrodes and said patient decreases the amplification of the respective amplifier means and for increasing the amplification thereof upon an increase in said common setting voltage,
   said amplifier means including means for controlling each other to produce equal output currents.

2. The apparatus as set forth in claim 1 wherein each of said sensing means including a respective transformer, each of said transformers having a primary winding and a secondary winding, the primary winding of each of said transformers being connected in series with the respective circuit including one of said pairs of said electrodes, said common controller means including a respective control line operatively connected to the respective amplifier means for amplification control thereof, respective resistors connected to each control line, respective rectifiers operatively connected to the secondary winding of a respective one of said transformers in each of said circuits and receiving a current-proportional voltage therefrom, said rectifiers being connected to respective ones of said resistors and thereby to the respective control line for feeding the latter voltage to the respective control line, respective second resistors for each circuit, a potentiometer acted on by D.C. voltage connected to said control lines via the respective second resistors whereby said difference voltage is produced on each control line and is used for the control of the amplification of respective amplifier means.

3. The apparatus as set forth in claim 2, which includes an amplifier disposed between the secondary winding of each of said transformers and said rectifiers.

4. The apparatus as set forth in claim 2, which includes a D.C. amplifier connected between each control line and the respective amplifier means.

5. The apparatus as set forth in claim 2, which includes an overvoltage indicating means connected to each of said control lines.

6. The apparatus set forth in claim 1 wherein said controller means includes a difference amplifier, means for applying said current — proportional voltage to one input of said difference amplifier, and means for applying said setting voltage to another input of said difference amplifier to form said difference voltage.

* * * * *